(12) United States Patent
Pfirrmann

(10) Patent No.: US 7,132,413 B1
(45) Date of Patent: Nov. 7, 2006

(54) ANTICOAGULANT/STERILIZING COMPOSITIONS AND METHODS

(75) Inventor: Rolf W. Pfirrmann, Lucerne (CH)

(73) Assignee: ED. Geistlich Soehne AG Fuer Chemische Industrie, Wolhusen (CH)

( * ) Notice: Subject to any disclaimer, the term of this patent is extended or adjusted under 35 U.S.C. 154(b) by 0 days.

(21) Appl. No.: 09/527,558

(22) Filed: Mar. 16, 2000

Related U.S. Application Data

(63) Continuation-in-part of application No. 09/493,797, filed on Jan. 28, 2000, which is a continuation of application No. PCT/GB98/02311, filed on Jul. 31, 1998.

(60) Provisional application No. 60/126,940, filed on Mar. 29, 1999.

(30) Foreign Application Priority Data

Jul. 31, 1997 (GB) ............................. 97162190.2

(51) Int. Cl.
  *A61K 31/727* (2006.01)
  *C07D 239/22* (2006.01)
(52) U.S. Cl. ..................... 514/56; 514/256
(58) Field of Classification Search ............ 514/56, 514/256; 422/58
See application file for complete search history.

(56) References Cited

U.S. PATENT DOCUMENTS

| 5,077,281 A | * | 12/1991 | Reinmuller ............... 514/56 |
| 5,167,960 A | * | 12/1992 | Ito et al. .................. 424/423 |
| 5,362,754 A | | 11/1994 | Raad et al. |
| 6,166,007 A | * | 12/2000 | Sodemann ............... 514/222.5 |

FOREIGN PATENT DOCUMENTS

| DE | 196 06 897 | 8/1997 |
| WO | 9828027 | 7/1998 |
| WO | WO 98/28027 | * 7/1998 |
| WO | WO 99/06114 | 2/1999 |
| WO | WO 00/01391 | 1/2000 |

OTHER PUBLICATIONS

J. Reinmüller, The Effect of Taurolidine on Physiological and Pathological Blood Coagulation and Implications for its Use, Zentralblatt für Chifurgie 1999, Suppl 4:13-18 (translation)-pp. 1-13.
British Pharmacopoeia 1998, vol. 2, Appendix XVIII, pp. A266-A267.
Blenkharn, J.I., "The Antimicrobial Activity of Taurolin®—A Possible Additive for Parenteral Nutrition Solutions," *Clinical Nutrition* (1987), vol. 6, No. 1, Feb. 1, 1987, pp. 35-38.
Jacobi, C.A. et al., "Intraperitoneal Instillation of Taurolidine and Heparin for the Prevention of Intraperitoneal Tumor Growth and Trocar Metastases in Laparoscopic Surgery in a Rat Model," *Langenbecks Arch Chir* (1997), vol. 382, No. 4, Suppl. 1, Jul. 25, 1997 pp. S31-S36.
Johnston, D.A. et al., "Taurolin for the Prevention of Parenteral Nutrition Related Infection: Antimicrobial Activity and Long-Term Use," *Clinical Nutrition* (1993), Dec. 1, 1993, vol. 12, No. 6, pp. 365-368.
Mughal, M., et al., "Infected Feeding Lines," *Care of Critically Ill*, Nov. 1, 1990, vol. 6, No. 6, pp. 228-231.

* cited by examiner

*Primary Examiner*—Leigh C. Maier
(74) *Attorney, Agent, or Firm*—Rothwell, Figg, Ernst & Manbeck, PC

(57) ABSTRACT

Compositions and methods are provided for preventing formation of thrombosis on a liquid-contacting surface of a liquid delivery system, such as a port, catheter or port-catheter system. The liquid delivery system is connected to a patient for delivery of a liquid to the patient. The method involves contacting the surface with a thrombosis-preventing liquid containing taurolidine, taurultam or a mixture thereof, the thrombosis-preventing liquid further containing an anticoagulant agent. In an alternative embodiment, the liquid-contacting surface of the delivery system is contacted with a solution containing an anticoagulant agent, and thereafter contacted with a solution containing taurolidine, taurultam or a mixture thereof.

13 Claims, No Drawings

ANTICOAGULANT/STERILIZING COMPOSITIONS AND METHODS

CROSS-REFERENCE TO RELATED APPLICATIONS

This application claims priority from U.S. Provisional application Ser. No. 60/126,940 filed Mar. 29, 1999, and is a continuation-in-part of U.S. patent application Ser. No. 09/493,797, filed Jan. 28, 2000, which is a continuation of PCT/GB98/02311, filed Jul. 31, 1998.

BACKGROUND OF THE INVENTION

1. Field of the Invention

The present invention relates to methods and compositions for preventing thrombosis in or caused by the use of liquid delivery systems, e.g., catheter and port systems.

2. Description of the Background Art

Delivery systems are widely used in medicine for introducing liquid material which might include medicaments, nutrition, or other active agents to a patient. Such systems frequently involve the use of catheters which, for many applications, are surgically or intravenously located and stitched into place for long-term administration of the desired material. Typical systems include central catheters such as may be used for total parenteral nutrition (TPN), e.g. when treating short bowel syndrome (for the duration of a patient's life), catheters and drains in hemodialysis and peritoneal dialysis for those with terminal kidney failure, and subcutaneously implanted port systems such as may be used in the treatment of malignant conditions.

One problem associated with the use of liquid delivery systems, e.g., port or catheter-based systems, is that these can give rise to infections which in turn may lead to infected intra-atrial thrombus, embolism, phlebitis, sepsis, endocarditis of the mitral valve, ostium infection, septic lung abscesses, and/or purulent septic pulmonary infarction. One solution to this problem is the use of solutions containing the antibacterial agents taurolidine and/or taurultam. For example, long term continuous infusion of taurolin solutions to prevent septic complications in patients receiving parenteral nutrition has been proposed (see Blenkharn, Clinical Nutrition 6(1):35–38, 1987 and Johnston et al., Clinical Nutrition 12(6): 365–358, 1993). More recently in WO98/28027, taurolin solutions have been suggested for use as a temporary seal or flush to prevent or reduce sepsis in port systems or catheters.

Taurolidine and/or taurultam are particularly effective in combating not only infecting bacteria but also in preventing the release of bacterial toxins as well as inactivating any that may be present. These compounds are methylol transfer agents and exert their antibacterial activity by reacting with the bacterial cell wall components and forming covalent bonds. Despite, therefore, the possibility of quite lengthy residence time in the delivery system, they have been found not to cause any build-up of resistance.

Another problem associated with the use of liquid delivery systems is the potential for blockage of the delivery tubes due to the formation of a coating of fibrin sheath deposits, especially during periods of long term use. The coating starts around a catheter with a thrombus containing fibrin, and progresses into vascularized, fibrous connective tissue. This sheath contains fibroblasts and collagen. Fibrinolytic agents cannot dissolve connective tissue.

Fibrin and/or collagen deposits can result in a significant narrowing of the delivery tubes and, in severe cases, total occlusion. The consequences of the formation of fibrin and/or collagen deposits in liquid delivery systems are therefore clearly dangerous. Moreover, removal or replacement of the delivery system may well have to be carried out operatively, necessitating a further stay in hospital for the patient and further expense.

Removal of a thrombus, especially when located at catheter closures, is difficult and cannot be resolved by fibrinolytic agents such as urokinase, streptokinase, etc., and the following complications are likely to occur. In cavacatheters complications may include thrombosis, embolism, phlebitis and sepsis. In femoral catheters complications may include thrombosis, lethal cases of pulmonary embolism and sepsis. In subclavial-catheters complications may include punctureproof blockage, thrombosis due to false catheter position, septic complications, total blockage of the vena subclava, and thrombotic changes caused by intima-damage (parietal thromboses between catheter- and vascular wall).

There remains a need in the art for methods and compositions for preventing thrombosis in liquid delivery systems.

SUMMARY OF THE INVENTION

In accordance with the present invention, a composition and method is provided for preventing thrombosis formation on a liquid-contacting surface of a liquid delivery system. The liquid delivery system is connected to a patient for delivery of a liquid to the patient. One embodiment involves contacting the surface with a thrombosis-preventing liquid containing taurolidine, taurultam or a mixture thereof, said thrombosis-preventing liquid further containing an anticoagulant agent. In an alternative embodiment, the liquid-contacting surface of the delivery system is contacted with a solution containing an anticoagulant agent, and thereafter contacted with a solution containing taurolidine, taurultam or a mixture thereof. The compositions of the invention may be utilized to carry out the above method.

DETAILED DESCRIPTION OF THE PREFERRED EMBODIMENTS

The compositions and methods of the present invention prevent thrombosis formation in liquid delivery systems such as catheter and port systems, including subcutaneous port systems for use in hemodialysis. Compositions in accordance with the present invention may include an antibactericidal-effective amount of a methylol transfer agent such as taurolidine and/or taurultam. The terms taurolidine and/or taurultam as used herein are intended to refer to the compounds taurolidine, taurultam, and there substantial bioequivalents. The taurolidine and/or taurultam preferably is present in a pharmaceutically-acceptable liquid, which in particularly preferred embodiments is an isotonic saline solution.

Compositions in accordance with the present invention may comprise a liquid containing a thrombosis-preventing amount of an anticoagulant agent. The anticoagulant may be, for example, sodium citrate or heparin. Other anticoagulants which may be included in compositions in accordance with the present invention and utilized with the inventive method include aprotinin, hirudin, desirudin, danaparoid, danaparoid-sodium, pentosan, pentosanpolysulfate-sodium, as well as thienopyridine derivatives such as ticlopidine, clopidogrel or the like, and mixtures thereof.

According to one embodiment, the inventive method provides a procedure to prevent deposits of thrombosis of fibrin and/or fibrin/collagen nets by combined application of taurolidine and/or taurultam in suitable isotonic or hypertonic solutions with added anticoagulant. This procedure serves to prevent catheter-sepsis and serious consequences for the patient. Also this combination serves to prevent catheter-blockage, thus avoiding risky surgical interventions for removal of thrombotic plugs (withdrawal of occlusions) or a change of catheters.

Desirudin, a recombinant hirudin, is an effective anticoagulant according to one embodiment, which in comparison to heparin works as a direct and selective inhibitor of free and fibrin-linked thrombin. The coagulation time of human plasma is prolonged by this agent. A dosage of a few mg added to a taurolidine solution, or a taurolidine/sodium-citrate solution is sufficient, e.g., about 0.1–10 mg, preferably about 1–2 mg.

Another coagulation inhibitor apart from heparin-sodium is danaparoid-sodium, an efficient antithrombotic agent including 84% of haparansulphate. This product is derived from porcine mucosa and due to purification steps is free from heparin and/or heparin fragments. This makes it very well tolerated and useful as an alternative to heparin-sodium in cases of heparin-induced thrombocytopenia. As a dosage, between about 7.5–15 anti-factor Xa units may be added to a 100 ml taurolidine solution.

Solutions with thrombocyte aggregation inhibitors or solutions which additionally contain anticoagulants such as citrate-dextrine solutions, citrate-phosphate-dextrose-adenin solutions, sodium citrate-citric acid solutions or heparin, etc., preferably should be filtered sterile after production and filled aseptically into vials of 10 to 100 ml. To avoid possible interactions between the added anticoagulants and taurolidine/taurultam, the inventive solutions can also be administered intermittently in two steps to avoid coagulation and formation of plaque in the catheter:

1) Instillation of sterile isotonic sodium chloride solution with anticoagulants. If desired, this solution can be aspired again.
2) Thereafter flushing of the catheter with sterile isotonic sodium chloride solution followed by instillation of the taurolidine 2% solution (lock-technique). If desired, the taurolidine solution can be aspired again after about one hour.

Viewed from one aspect, the invention thus provides a solution suitable for use in a liquid delivery system, e.g., port or catheter-based systems, including hemodialysis systems, comprising taurolidine and/or taurultam in combination with an anticoagulant.

Preferred solutions will contain from 0.5 to 3% by weight of taurolidine, or from 1 to 7.5% by weight taurultam, advantageously 3 to 5%, depending on the solubility of the compound. Solutions containing from 1.0 to 2.0%, preferably about 1.0% by weight, taurolidine are preferred.

Sodium citrate may be used in the form of anhydrous sodium citrate, but preferably will be used in the form of the dihydrate. Preferred solutions are those containing 0.5 to 3.0% by weight, preferably 1.0 to 2.0%, sodium citrate. Solutions containing about 1.5% by weight, e.g., 1.45% sodium citrate have been found to be isotonic without the need for additional electrolytes and are particularly preferred for use in the invention.

In one embodiment of the invention, the solutions may contain heparin, a heparin derivative or an analog, e.g., pentosan-sodium, in particular heparin-Na or heparin-Ca. The desired amount of heparin will vary from patient to patient but can nevertheless be readily determined by those skilled in the art. An average concentration of heparin can be expected to be in the range of from to 1 to 15 U/ml heparin-Na, preferably 1 to 2 U/ml.

The solutions in accordance with the invention will generally be made up in sterile pyrogen-free water and may also contain, for example, inorganic or other salts or other components to render them isotonic. Cations and anions such as sodium, potassium, calcium, chloride, lactate, maleate and bicarbonate are suitable for use as electrolytes. Sodium chloride is particularly suitable, e.g., in an amount of about 0.45% by weight.

Parenterally acceptable polyols may, for example, also be present since these have been observed to increase the overall intravenous tolerance of taurolidine. Suitable polyols include carbohydrates, e.g., hexoses such as glucose and fructose (or mixtures of these such as invert sugar), pentoses such as xylose or polysaccharides such as dextran or hydrolyzed starch; glycerol and sugar alcohols such as sorbitol, mannitol or xylitol.

The concentration of the polyol can usefully be in the range 3 to 40% by weight. In the case of glucose, the concentration may be in the range 10 to 30% by weight, preferably 20%.

The solutions may also contain polyvinylpyrrolidone (PVP). This may be incorporated into the solutions at a concentration of, e.g. from 4 to 7% by weight. A solution containing 5% PVP is preferred. This assists in solubilizing the active substance and contributes also to the oncotic pressure of the solution. The molecular weight of the PVP should not be greater than 50,000 and is preferably less than 10,000, for example between 7,000 and 9,000. Kollidone 17 as sold by BASF, specially purified (substantially free of peroxide as taught in PCT/GB97/00069) is relatively quickly resorbed and excreted renally.

The pH of the solution will preferably be in the range 7 to 8, e.g. about 7.3–7.4. While any component present in the solution may itself serve to yield a solution with the desired pH, conventional buffers or pH adjusting agents may be used.

Such solutions are used in accordance with the present invention in conjunction with liquid delivery systems, e.g., catheters and port systems. Such solutions may conveniently be used to fill, flush out or seal the delivery system when not in use. Preferably, these may be used to effectively seal the delivery system between each administration of desired liquid material, such as chemotherapeutic agent or nutrient, or after withdrawal of any blood sample from the reservoir. Should there be any period of time when it is desired not to use the delivery system for administration of chemotherapeutic or other active or nutritional agent, such as is often the case during the cyclical delivery of chemotherapeutic agents or during total parenteral nutrition, the delivery system can be filled with a solution in accordance with the invention to act as an antimicrobial seal. Relatively small volumes (of the order of a few milliliters, e.g. approximately 3 ml) of the solution are required for this. A contact time of about one hour is desirably a minimum, though the seal can be retained for up to twelve hours or more. According to one embodiment, a solution in accordance with the present invention is sealed within the liquid delivery system for at least about 12 hours. A solution in accordance with the present invention which is sealed in the liquid delivery system can be replaced daily. All of these activities can be carried out without any development of resistance or build-up of bacterial toxins such as LPS and exotoxins by resident bacteria. Solutions in accordance with the invention are well tolerated in vivo; there is no toxicity and no side effects have been observed.

Accordingly, viewed from a further aspect the invention provides the use of a solution as herein described as a temporary seal to prevent or reduce blood coagulation in a liquid delivery system. This is of particular application to the use of catheters.

Viewed from another aspect the invention provides the use of a solution as herein described to reduce or prevent blood coagulation associated with the use of subcutaneously-implanted delivery systems.

The solutions of the invention are of particular application to systems which deliver medication from a reservoir via a catheter into the cardiovascular system, such as might be used during chemotherapy. Prior to introducing a cancer chemotherapeutic agent, for example, the taurolidine solution in accordance with the invention (present as a temporary seal) is removed from the catheter or rinsed into the bloodstream using saline. Cancer chemotherapeutic agent as desired is then injected into the chamber and enters into the body over a period of time. Examples of possible such agents include the alkylating agents, such as numistin hydrochloride and cyclophosphamide; antimetabolites such as fluorouracil, cytarabine and methotrexate; anti-tumor antibiotics such as bleomycin sulphate, daunorubicin hydrochloride and idarubicin hydrochloride; alkaloids such as lincristine sulphate and cisplatins such as carboplatin. These agents are administered via the port system in different formulations for several short-term and long-term infusions or for bolus injections.

Viewed from a yet further aspect, the invention provides a method of inhibiting blood coagulation in or associated with the use of a liquid delivery system, e.g., a port or catheter-based system including a hemodialysis system in which the system is flushed and/or sealed with a solution according to the invention in an amount effective to inhibit blood coagulation.

As indicated above, according to one embodiment, the anticoagulant for use in the present invention is administered as a combined preparation with the taurolidine and/or taurultam solution. However, depending on the nature of the treatment, in other embodiments the anticoagulant solution is administered separately, prior to, during or subsequent to administration of taurolidine and/or taurultam solution.

For example, in one embodiment the liquid delivery system is first contacted with a solution containing a thrombosis-preventing amount of an anticoagulant as indicated above, for example, by flushing the device with the anticoagulant solution or injecting the anticoagulant solution into the device and then removing the anticoagulant solution, e.g., by aspiration or flushing. Thereafter, a solution containing taurolidine is instilled into the liquid delivery system and preferably held in contact with the internal surfaces thereof for at least about 1 hour.

A particular advantage of the combination of taurolidine, taurultam, sodium citrate and/or organic anticoagulant for thrombus prevention in a catheter system, and also for infection prevention, lies in the unexpectedly small quantities of anticoagulant required, i.e., respectively few milligrams per hundred milliliters are required to prevent fibrin/collagen deposits within the catheter system.

The combination solution has proven to be unexpectedly advantageous for stability of the product, with the combination solution being sterile-filtered with 0.1–0.2 μm filters and thereafter aseptically filled into 10–100 ml serum bottles.

It is also possible to sterilize bottles filled with combination solution over a short term with steam, sufficient to inactivate any microorganisms (bioburden) present, without inactivating or substantially reducing the anticoagulation properties of the product.

When anticoagulants are utilized which do not tolerate heat sterilization, the solution in accordance with the invention may be filtered under aseptic conditions through a filter having sufficiently small pores so as to sterilize the solution, e.g., a 0.1–0.2 micron sterile filter. The thus-filtered solutions then may be filled into 10–100 ml viles or bottles and sealed with a rubber stopper and aluminum cap.

Viewed from another aspect the invention thus provides products containing a solution of taurolidine and/or taurultam and a solution containing an anticoagulant selected from sodium citrate, aprotinin, hirudin, desirudin, danaparoid, danaparoid-sodium, heparin, pentosan, pentosanpolysulfate-sodium, as well as thienopyridine derivatives such as ticlopidine, clopidogrel and the like, and mixtures thereof. Low dosages of anticoagulant can be utilized, e.g., about 0.1–10 mg, preferably about 1–2 mg.

A thrombosis-preventing liquid in accordance with the present invention may contain an anticoagulant material as described above present in the solution in an amount within a range of from about 0.01 to about 5% by weight.

Although the invention has been described with particular reference to the use of taurolidine and/or taurultam in liquid delivery systems, the specific anticoagulants herein described may be utilized in preventing the formation of fibrin collagen deposits in liquid delivery systems, especially within the delivery tubes.

Thus, the invention provides the use of an anticoagulant as herein described to prevent blood coagulation in a liquid delivery system, e.g., a port or catheter-based system.

The invention will be further illustrated by way of the following non-limiting examples.

EXAMPLE 1

2% taurolidine solution and 3% taurolidine solution is prepared in accordance with the present invention as follows.

| 2% Taurolidine Solution | | |
| --- | --- | --- |
| Substance | Percent by weight | Amount per liter |
| Taurolidine | 2.0 | 20 g |
| Trisodium citrate dihydrate | 3.0 | 30 g |
| Water | 95.0 | Adjust to 1 L |
| Citric acid monohydrate | 0.024 | 240 mg |
| Total | 100.0 | 1 liter | pH 7.0–7.2 after sterilization

The taurolidine and trisodium citrate dihydrate are dissolved in the water at up to 60° C., cooled down, and the pH adjusted to 7.4 with the citric acid monohydrate and sodium hydroxide. The solution is sterile filtered, filled into 10–100 ml serum bottles. To avoid undesirable interactions, sterilization should preferably be done quickly and below 121° C., in relation to the bioburden and the $F_o$ concept as described, for example, in the British Pharmacopoeia 1998, Appendix XVIII.

| 3% Taurolidine Solution | | |
|---|---|---|
| Substance | Percent by weight | Amount per liter |
| Taurolidine | 3.0 | 30 g |
| Trisodium citrate dihydrate | 3.0 | 30 g |
| Water | 94.0 | Adjust to 1 l |
| Citric acid monohydrate | 0.024 | 245 mg |
| Total | 100.0 | 1 liter | pH 7.0–7.2 after sterilization

The taurolidine and trisodium citrate dihydrate are dissolved in the water at up to 60° C., cooled down, and the pH adjusted to 7.0–7.2 with the citric acid monohydrate. The solution is sterile filtered, aseptically filled into 10–100 ml serum bottles.

To each of the above formulations may be added one or more of the following anticoagulants:

Heparin-sodium

Aprotinin

Hirudin

Heparin

Pentosan-sodium

Desirudin

Danaparoid-sodium

If separately prepared, the above components are dissolved in the distilled water, sterile filtered, filled into bottles and autoclaved in accordance with bioburden for 15 mins at 100–121° C.

EXAMPLE 2

Port Delivery System

A patient has a port delivery system comprising a polyurethane chamber of approx. 0.5 cm$^3$ volume mounted on a small titanium plate implanted in a small pocket in the pectoral muscle. The tip of a catheter of approx. 0.3 mm diameter leading from it has been intubated into one of the major veins and lies close to the point of entry of the vena cava into the right atrium of the heart. After implantation the chamber was flushed through with 2 ml of a sterile 0.9% by weight sodium chloride solution containing 800 I.U. heparin.

The chamber is then filled with approximately 3 ml of a solution according to Example 1 (injected into the chamber by special syringe). The device is then sealed for up to 12 hours or until whenever chemotherapeutic administration is due.

After each treatment with medication, or after use of the chamber to withdraw a sample of venous blood, the delivery system is rinsed meticulously with 10 ml of a sterile 0.9% sodium chloride solution. 2 ml of a solution according to Example 1 are then introduced into the chamber and the needle removed. The port system is then effectively sealed against microbial infection. After being rinsed with saline, further medication may then be introduced when desired and the cycle repeated. Alternatively, the instilled solution can be aspired before further medication is introduced.

EXAMPLE 3

Catheter Delivery System

A patient undergoing total parenteral nutrition is fitted with a central catheter by known techniques. Nutrition is delivered overnight while the patient is asleep but during the day the catheter is sealed with approximately 3 ml of a solution according to Example 1.

This is effective to prevent catheter sepsis and to prevent fibrin and/or collagen deposits within the delivery tubes. Moreover, this has no side effects when it passes into the body when nutrition recommences possibly several hours later overnight.

The invention claimed is:

1. A method of preventing thrombus formation on a liquid-contacting surface of a liquid delivery system, the liquid delivery system being connected to a patient for delivery of a liquid to said patient, the method comprising first contacting said surface with a solution containing a thrombus-preventing amount of an anticoagulant agent other than taurolidine or taurultam, thereafter contacting said surface with a solution containing taurolidine, taurultam or a mixture thereof, and repeating both of the surface contacting steps between delivery of liquids to said patient.

2. The method of claim 1 wherein the solution containing taurolidine, taurultam or mixture thereof is contacted with said surface for at least about 1 hour.

3. The method of claim 2 wherein said solution containing taurolidine, taurultam or mixture thereof is sealed in said delivery system for a period of at least 12 hours.

4. The method of claim 3 wherein said solution containing taurolidine, taurultam or mixture thereof which is sealed in said delivery system, is replaced at least about daily.

5. The method of claim 1 wherein the anticoagulant-containing solution is contacted with said surface by injecting the anticoagulant-containing solution into said liquid delivery system and then removing said anticoagulant-containing solution from said liquid delivery system.

6. The method of claim 5 wherein the solution containing taurolidine, taurultam or a mixture thereof is contacted with said surface for at least about 1 hour.

7. The method of claim 6 wherein said solution containing taurolidine, taurultam or a mixture thereof is sealed in said delivery system for a period of at least about 12 hours.

8. The method of claim 7 wherein the solution containing taurolidine, taurultam or a mixture thereof which is sealed in said delivery system is replaced at least about daily.

9. The method of claim 1 wherein said solution containing taurolidine, taurultam or a mixture thereof contains from about 0.5 to about 3% by weight of taurolidine, or from about 1 to about 7.5% by weight of taurultam.

10. The method of claim 1 wherein said anticoagulant agent is selected from the group consisting of sodium citrate, aprotinin, hirudin, desirudin, danaparoid, danaparoid-sodium, heparin, pentosan, pentosanpolysulfate-sodium, ticlopidine, clopidogrel, and mixtures thereof.

11. The method of claim 10 wherein said anticoagulant agent is present in an amount within a range of from about 0.1–10 mg.

12. A method of preventing thrombus formation on a liquid-contacting surface of a liquid delivery system, the liquid delivery system being connected to a patient for delivery of a liquid to said patient, the method comprising first contacting said surface with a solution containing a thrombus-preventing amount of an anticoagulant agent other than taurolidine or taurultam, thereafter contacting said surface with a solution containing taurolidine, taurultam or a mixture thereof, and further conducting both of the surface contacting steps between subsequent delivery of liquids to said patient.

13. A method of preventing thrombus formation on a liquid-contacting surface of a liquid delivery system, the liquid delivery system being connected to a patient for delivery of a liquid to said patient, the method comprising first contacting said surface with a solution containing a thrombus-preventing amount of an anticoagulant agent other than taurolidine or taurultam, thereafter contacting said surface with a solution containing taurolidine, taurultam or a mixture thereof, and further conducting the surface contacting step with the solution containing taurolidine, taurultam or a mixture thereof between subsequent delivery of liquids to said patient.

* * * * *